US00PP22020P2

(12) United States Plant Patent
Heuger

(10) Patent No.: US PP22,020 P2
(45) Date of Patent: Jul. 5, 2011

(54) ***HELLEBORUS* PLANT NAMED 'HLR 180'**

(50) Latin Name: *Helleborus orientalis hybrid*
Varietal Denomination: HLR 180

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 12/798,345

(22) Filed: Mar. 31, 2010

(51) Int. Cl.
*A01H 5/00* (2006.01)

(52) U.S. Cl. ..... Plt./439

(58) Field of Classification Search ..... Plt./439
See application file for complete search history.

*Primary Examiner* — Annette H Para
(74) *Attorney, Agent, or Firm* — C. A. Whealy

(57) ABSTRACT

A new and distinct cultivar of *Helleborus* plant named 'HLR 180', characterized by its upright and outwardly arching plant habit; uniform flowering habit; long flowering period; single white-colored flowers with red purple-colored central spots; and good garden performance.

2 Drawing Sheets

Botanical designation: *Helleborus orientalis* hybrid.
Cultivar denomination: 'HLR 180'.

BACKGROUND OF THE INVENTION

The present invention relates to a new and distinct cultivar of *Helleborus* plant, botanically known as *Helleborus orientalis* hybrid, and hereinafter referred to by the name 'HLR 180'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in November, 2002 of two unnamed proprietary seedling selections of *Helleborus orientalis* hybrid, not patented. The new *Helleborus* plant was discovered and selected by the Inventor as a single flowering plant from within the progeny of the stated cross-pollination grown in a controlled greenhouse environment in Glandorf, Germany in February, 2005.

Asexual reproduction of the new *Helleborus* plant by divisions in a controlled greenhouse environment in Glandorf, Germany since March, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'HLR 180'. These characteristics in combination distinguish 'HLR 180' as a new and distinct cultivar of *Helleborus* plant:

1. Upright and outwardly arching plant habit.
2. Uniform flowering habit.
3. Long flowering period.

4. Single white-colored flowers with red purple-colored central spots.
5. Good garden performance.

Compared to plants of the parent selections, plants of the new *Helleborus* flower more freely and more uniformly.

Plants of the new *Helleborus* can be compared to plants of *Helleborus orientalis* hybrid 'HGC Merlin', disclosed in U.S. Plant Pat. No. 15,705. Plants of the new *Helleborus* differ primarily from plants of 'HGC Merlin' in the following characteristics:

1. Plants of the new *Helleborus* have larger flowers than plants of 'HGC Merlin'.
2. Flowers of plants of the new *Helleborus* are white in color with red purple-colored central spots whereas flowers of plants of 'HGC Merlin' are dark purple in color.

BRIEF DESCRIPTION OF THE PHOTOGRAPHS

The accompanying colored photographs illustrate the overall appearance of the new *Helleborus* plant, showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'HLR 180' grown in a container.

The photograph on the second sheet is a close-up view of a typical flower of 'HLR 180'.

DETAILED BOTANICAL DESCRIPTION

The aforementioned photographs and following observations, measurements and values describe plants grown in Glandorf, Germany in 1.5-liter containers during the winter in a glass-covered greenhouse and under conditions which closely approximate commercial *Helleborus* production. During the production of the plants, day temperatures ranged from 12° C. to 32° C. and night temperatures ranged from 3° C. to 18° C. Plants were one year old when the photographs and the description were taken. In the following description, color references are made to The Royal Horticultural Society Colour Chart, 2007 Edition, except where general terms of ordinary dictionary significance are used.

Botanical classification: *Helleborus orientalis* hybrid 'HLR 180'.

Parentage:

*Female, or seed, parent.*—Unnamed proprietary seedling selection of *Helleborus orientalis* hybrid, not patented.

*Male, or pollen, parent.*—Unnamed proprietary seedling selection of *Helleborus orientalis* hybrid, not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright and outwardly arching plant habit; shape, globular; moderately vigorous growth habit.

*Plant height.*—About 29.8 cm.

*Plant diameter* (*area of spread*).—About 45.2 cm.

Foliage description:

*Arrangement.*—Leaves arranged in a basal rosette; palmately compound with five leaflets per leaf.

*Leaf length.*—About 12.6 cm.

*Leaf width.*—About 16.4 cm.

*Leaflet length.*—About 8.6 cm.

*Leaflet width.*—About 3.5 cm.

*Leaf shape.*—Palmate; orbicular in outline.

*Leaflet shape.*—Elliptic to narrowly obovate; lowest leaflets typically cleft.

*Leaflet apex.*—Acute.

*Leaflet base.*—Attenuate.

*Leaflet margin.*—Finely serrate.

*Leaflet texture, upper and lower surfaces.*—Smooth, glabrous; leathery.

*Leaflet venation pattern.*—Pinnate.

*Leaflet color.*—Developing leaves, upper surface: Slightly darker than 144A. Developing leaves, lower surface: Close to 144A. Fully developed leaves, upper surface: Between 147A and 139A; at the base, close to N186C; venation, close to 144C. Fully developed leaves, lower surface: Close to 146B; at the base, close to N186C; venation, close to 144C.

*Petiole.*—Length: About 14.8 cm. Diameter: About 4 mm. Texture, upper and lower surfaces: Smooth, glabrous. Color, upper and lower surfaces: Close to 144A; at the base and apex, tinged with between 177A, N186C and 187A.

Flower description:

*Flower shape and habit.*—Single rotate flowers; uniform flowering habit; about five flowers per terminal cyme; flowers facing slightly outwardly to nodding.

*Fragrance.*—None detected.

*Natural flowering season.*—Long flowering period; plants flower from winter to early spring in Germany.

*Flower longevity on the plant.*—About ten days; flowers not persistent.

*Flower buds.*—Length: About 2.1 cm. Diameter: About 1.4 cm. Shape: Ovate. Color: Close to 157A, spots, close to 182C to 182D; at the base, close to 144B.

*Inflorescence height.*—About 29.8 cm.

*Inflorescence diameter.*—About 12.3 cm.

*Flower diameter.*—About 6.7 cm.

*Flower depth* (*height*).—About 2.1 cm.

*Petals.*—Transformed into nectaries.

*Sepals.*—Arrangement: About five in a single whorl. Length: About 3.5 cm. Width: About 3.1 cm. Shape: Broadly ovate to broadly elliptic. Apex: Broadly acute. Margin: Entire. Texture, upper and lower surfaces: Smooth, glabrous. Color: When opening, upper surface: Close to NN155C; central spots, close to 186A to 187C to 187D; towards the base, close to 145C. When opening, lower surface: Close to NN155B to NN155C; faint central spots, close to 182C to 182D; towards the base, close to 145C to 145D. Fully opened, upper surface: Close to NN155B to NN155C; central spots, close to 187C to 187D; towards the base, close to 145C; with development, color becomes closer to 145B to 145C with central spots, close to 187C. Fully opened, lower surface: Close to NN155B to NN155C; faint central spots, close to 182C to 182D; towards the base, close to 145C to 145D.

*Peduncles.*—Strength: Moderately strong. Length: About 18.7 cm. Diameter: About 6 mm. Aspect: About 15° from vertical. Texture: Smooth, glabrous. Color: Close to 145B.

*Pedicels.*—Strength: Moderately strong. Length: About 1.8 cm. Diameter: About 2 mm. Aspect: About 20° from the peduncle axis. Texture: Smooth, glabrous. Color: Close to 145B.

*Reproductive organs.*—Stamens: Quantity per flower: About 90. Filament length: About 1.1 cm. Filament color: Close to 157A. Anther shape: Narrowly reniform. Anther length: About 2.5 mm. Anther color: Close to 155A. Pollen amount: Moderate. Pollen color: Close to 158D. Pistils: Quantity per flower: About five. Pistil length: About 1.2 cm. Stigma shape: Club-shaped. Stigma color: Close to 157D. Style length: About 1.2 cm. Style color: Close to 144A to 144B. Ovary color: Close to 150B to 150C. Nectaries (transformed petals): Quantity per flower: About 14. Length: About 7 mm. Diameter, apex: Close to 3.5 mm. Diameter, base: Close to 1 mm. Shape: Flattened triangular. Color: Close to 144B.

*Seeds/fruits.*—Seed and fruit development have not been observed.

Garden performance: Plants of the new *Helleborus* have been observed to have good garden performance and to tolerate rain, wind and temperatures ranging from about −10° C. to about 35° C.

Pathogen/pest resistance: Plants of the new *Helleborus* have not been shown to be resistant to pathogens and pests common to *Helleborus*.

It is claimed:

1. A new and distinct *Helleborus* plant named 'HLR 180' as illustrated and described.

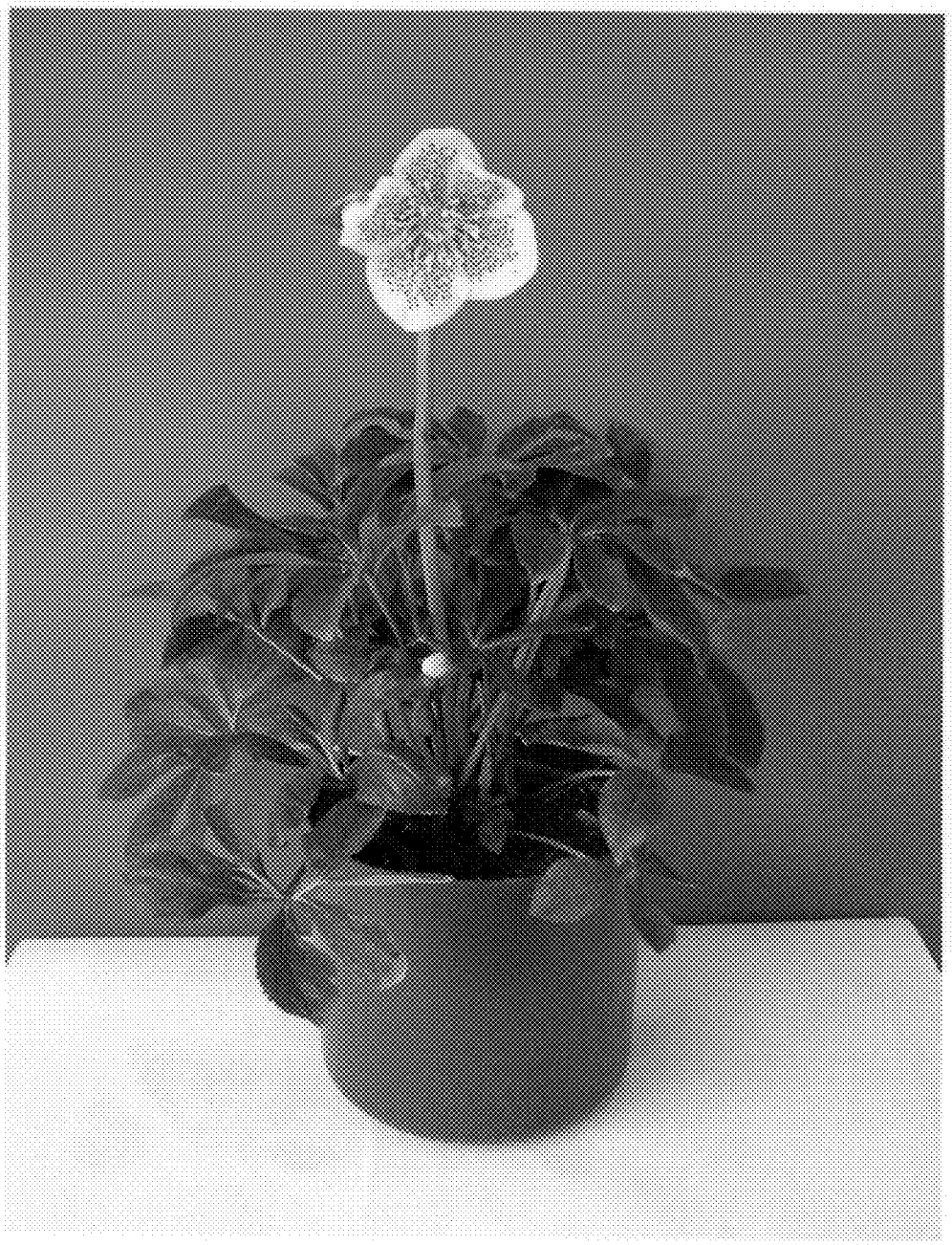

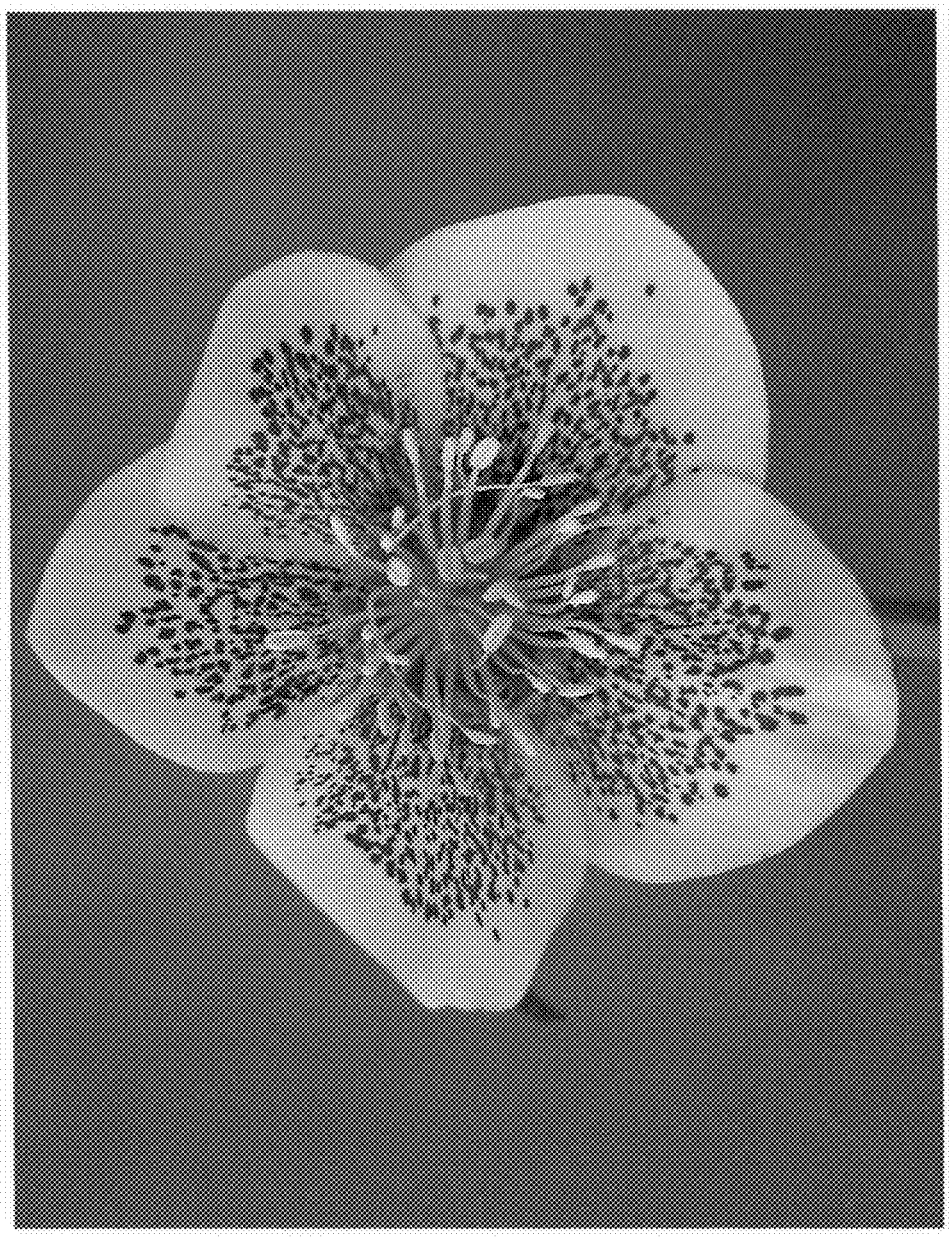

* * * * *